United States Patent [19]
Dong et al.

[11] Patent Number: 5,814,820
[45] Date of Patent: Sep. 29, 1998

[54] PUMP PROBE CROSS CORRELATION FLUORESCENCE FREQUENCY DOMAIN MICROSCOPE AND MICROSCOPY

[75] Inventors: Chen-Yuan Dong; Enrico Gratton; Peter So, all of Urbana, Ill.

[73] Assignee: The Board of Trustees of the University of Illinois, Urbana, Ill.

[21] Appl. No.: 599,256

[22] Filed: Feb. 9, 1996

[51] Int. Cl.[6] .................................................. G01N 21/64
[52] U.S. Cl. .................................... 250/458.1; 250/461.1; 250/161.2
[58] Field of Search ............................ 250/461.2, 461.1, 250/458.1

[56] References Cited

U.S. PATENT DOCUMENTS

| | | | |
|---|---|---|---|
| 3,013,467 | 12/1961 | Minsky | 356/423 |
| 3,853,398 | 12/1974 | Kano | 355/43 |
| 4,312,330 | 1/1982 | Holdridge | 126/698 |
| 4,884,881 | 12/1989 | Lichtman et al. | 359/227 |
| 5,022,757 | 6/1991 | Modell | 356/318 |
| 5,034,613 | 7/1991 | Denk et al. | 250/458.1 |
| 5,151,869 | 9/1992 | Alcala | 364/492 |
| 5,162,941 | 11/1992 | Favro et al. | 359/386 |
| 5,234,457 | 8/1993 | Andersen | 606/198 |
| 5,235,457 | 8/1993 | Lichtman et al. | 359/368 |
| 5,254,857 | 10/1993 | Ross et al. | 250/310 |
| 5,293,213 | 3/1994 | Klein et al. | 356/349 |
| 5,294,799 | 3/1994 | Aslund et al. | 250/458.1 |
| 5,296,703 | 3/1994 | Tsien | 250/235 |
| 5,371,624 | 12/1994 | Nagano et al. | 359/389 |

OTHER PUBLICATIONS

"Pump/probe method for fast analysis of visible spectral signatures utilizing asynchronous optical sampling", Paul A. Elzinga, Ronald J. Kneisler, Fred E. Lytle, Yanan Jiang, Galen B. King, and Normand M. Laurendeau, Applied Optics, vol. 26, No. 19, Oct. 1987.

"An Introduction to Time–Resolved Pump/Probe Spectroscopy", F.E. Lytle, R.M. Parrish and W.T. Barnes, Appl. Spectroscopy, vol. 39, No. 3, 1985, pp. 444–451.

"Pump/Probe Spectroscopy by Asynchronous Optical Sampling". P.A. Elzinga, F.E. Lytle, Y. Jiang G. B King, and N.M. Laurendeau, Appl. Spectroscopy, vol. 41, No. 1, 1987.

*Primary Examiner*—Constantine Hannaher
*Attorney, Agent, or Firm*—Greer, Burns & Crain, Ltd.

[57] ABSTRACT

A scanning fluorescence lifetime microscope measures modulation and phase in fluorescence emission stimulated by spatially overlapped pump and probe beams operating at different frequencies. A pump laser modulated at a first frequency is focused onto a diffraction limited spot to excite a fluorescent sample under study. Simultaneously, a probe laser modulated at a second frequency is focused onto the same spot to induce a stimulated fluorescence emission in response to the optically combined output of the pump and probe laser light. Fluorescence emitted from the sample produces a cross-correlation signal which is dependent upon the spatial overlapping of the pump and probe beams at the focal point thereby producing a beneficial axial sectioning effect. Choosing a small difference frequency between the modulation of the first and second laser sources produces a low frequency cross correlation signal even when the modulation frequencies of the pump and probe lasers are very high. A signal processor obtains modulation and phase information from the low frequency cross correlation fluorescence signal allowing monitoring of even ultrafast fluorescence phenomena induced by high frequency modulation of the pump and probe lasers.

18 Claims, 11 Drawing Sheets
(4 of 11 Drawing(s) Filed in Color)

FIRST HARMONIC AMPLITUDE 0            1

PHASE 45            80

FIRST HARMONIC AMPLITUDE

ONE-PHOTON IMAGE

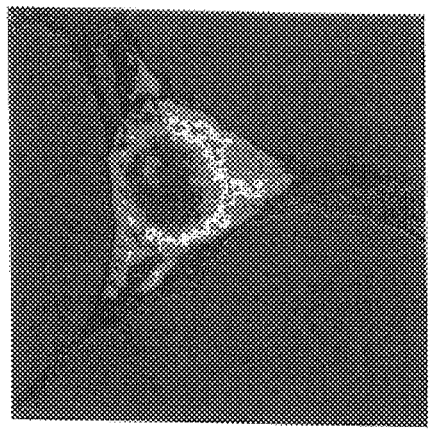
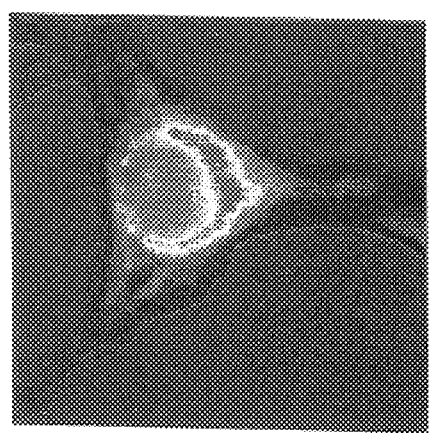
FIG. 6c
FIG. 6d

FIRST HARMONIC AMPLITUDE 0                          1

PHASE 0                          90

PUMP PROBE CROSS CORRELATION FLUORESCENCE FREQUENCY DOMAIN MICROSCOPE AND MICROSCOPY

This invention was made with Government support under grant number PHS-5RR03155 awarded by the National Institute of Health. The Government has certain rights in this invention.

BACKGROUND OF THE INVENTION

The present invention relates generally to a microscope which provides excellent spatial resolution, rejects background fluorescence generated from off-focal planes, and images at high modulation frequencies. More particularly, the present invention relates to a microscope in which a modulated laser source is used to excite a sample and another spatially overlapping modulated laser source is used to induce a stimulated emission thereby producing a low frequency cross-correlation signal which is monitored to produce image data indicative of fluorescence emission lifetime.

A physical reaction in which a sample, such as a fluorescently labelled biological cell, absorbs light and after a period of time emits fluorescence is the primary basis for what is generally known as fluorescence microscopy. An excited molecule, or chromophore, emits fluorescence when it returns to ground state after having been excited by being subjected to light. Some samples, known as autofluorescent samples, naturally undergo such a reaction. Other samples may be stained to permit the excitation and relaxation of chromophores.

Fluorescence microscopes take advantage of this physical reaction by monitoring the fluorescence emitted when a chromophore returns to its ground state after having been excited. Scanning fluorescence microscopy is applicable to study subjects including semiconducting devices and biological cells. Generally known fluorescence microscopes subject a sample to light which induces absorption of a photon. Dissipation of the excess energy results in fluorescence emissions in autofluorescent or stained samples. The fluorescence emissions are monitored by an optical sensor, such as a photomultiplier. Altering the positional relationship between the sample and the focused combined light to produce a raster scan effect allows information concerning the sample structure and positional relationship within the structure to be obtained by monitoring fluorescence amplitude in the time domain.

Standard fluorescence microscopes suffer from poor spatial resolution arising primarily because the optical detector is unable to reject off-focal fluorescence. Off focal fluorescence combines with the fluorescence emitted in response to the light focused upon the desired spot, and adversely affects the spatial resolution of the optical detection portion of the system. In addition, the inability of standard fluorescence microscopy techniques to reject off focal fluorescence also prevents the systems from obtaining three dimensional sectional information. Accordingly, only thin samples may be effectively investigated through the standard fluorescence microscope systems, and the spatial resolution provides rough detail concerning positional relationships within the sample structure.

Recently, spatial resolution difficulties encountered in fluorescence microscopes have been addressed through improved microscopy systems including confocal scanning microscopes and two-photon scanning microscopes. These microscopes seek to reject fluorescence from off focal planes to improve spatial resolution.

In the confocal microscope systems, a spatial filter is placed in front of the optical sensor. This filter takes the form of a transmissive pin-hole in an otherwise opaque surface which prevents off focal fluorescence from impinging upon the optical sensor. Because off-focal fluorescence does not reach the optical sensor, spatial resolution of the microscope system is improved. The rejection of off focal fluorescence also enables the confocal systems to realize depth discrimination and produce 3-D image sectioning by altering the focal depth through relative displacement between the sample and an objective lens used to focus excitation light upon the sample.

An alternative technique to improve spatial resolution and enable 3-D sectioning is two photon fluorescence microscopy, such as that in U.S. Pat. No. 5,034,613 to Denk et al. In a two photon microscope system, molecular excitation is produced in a sample by focusing high power pulsed laser light to induce simultaneous absorption of two photons. High photon density is created at the focal point to induce two photon excitation of chromophores. Excitation rates, as well as fluorescence rates, in the sample are proportional to the square of the intensity of the incident light. This dependence achieves a reduction in off focal fluorescence even when a pin hole is not used to spatially filter fluorescence directed toward the optical sensor.

A difficulty encountered in the confocal microscope systems concerns the need for precise mechanical alignment. The pin hole of the spatial filter must be exactly aligned to pass the desired fluorescence to the optical sensor. While the two-photon microscope overcomes this alignment difficulty, expensive picosecond or femtosecond modulated lasers are necessary to produce the simultaneous two photon absorption.

For many years the primary parameter used to characterize sample structures being studied using various types of fluorescence microscopy was the intensity of the induced fluorescence signal. Useful information is also available from studying the dynamics within sample occurring over a predetermined time. In molecular cell study, dynamic processes affecting lifetimes of chromophores inside cells include rotation of probe molecules in membranes, collisional (dynamic) quenching of probe molecule lifetime, and energy transfer from excited state chromophores to surrounding molecules. For instance, quenching may result from collisions between excited state chromophores and quencher molecules (dynamic quenching) or from the formation of complexes with the chromophore (static quenching). Through measurement of fluorescence lifetimes, a fluorescence microscope system may distinguish between dynamic and static quenching to provide useful information concerning sample dynamics. Static quenching tends to decrease the concentration of potential chromophores, without affecting fluorescence lifetimes, whereas dynamic quenching tends to reduce fluorescence because the collisions reduce population of excited chromophores by a means other than fluorescence. Lifetime monitoring may also distinguish between chromophores having similar emission intensity emission spectra, but distinct lifetimes.

These dynamic processes can be examined by monitoring fluorescence induced in response to a sinusoidally modulated excitation laser. Finite lifetime of the sample results in a fluorescence signal which is delayed in phase and is intensity demodulated. Considering a fluorescent sample having a single exponential lifetime $\tau$ excited by a sinusoidal modulated laser of frequency $\omega$, the fluorescence density in spatial (r) and temporal (t) coordinates F(t) obeys the following differential equation:

$$\frac{dF(r, t)}{dt} = -\frac{1}{\tau} F(r, t) + I(r, t) \quad (1)$$

where $I(r,t)=[1+m_e\sin(\omega t)]\, I(r)$ is the excitation function.

The integrated fluorescence intensity responds at the same circular frequency $\omega$ but at a different phase $\phi$ and modulation $m_f$:

$$F(t) \alpha c \sigma q [1+m_f \sin(\omega t+\phi)] \int I(r) d^3 r \quad (2)$$

where c is the concentration of chromophores assumed to be constant, $\sigma$ is the absorption cross-section, and q is the quantum yield. In solving Eqns. (1) and (2), two independent determinations of the lifetime $\tau_p$ (phase) and $\tau_m$ (modulation) are obtained:

$$\tan(\phi) = \omega \tau_p \text{ and } m = \frac{m_f}{m_c} = \frac{1}{\sqrt{1 + \omega^2 \tau_m^2}}. \quad (3)$$

Since lifetime of a typical chromophores is on the order of a nanosecond lifetime imaging of cells is required to obtain useful information concerning the phase and modulation.

In a typical fluorescent microscope system, such as a confocal or two-photon microscope, response times of the optical sensors will set the order of magnitude of imaging response temporal resolution. A conventional inexpensive photomultiplier tube used in such systems, for instance, typically may be gain modulated to about 300 MHz allowing study of dynamic processes having a temporal resolution of 100 ps. When the detector is subjected to higher frequency fluorescence phenomena the limited ability of the optical detector to sense fluorescence of short duration limits the temporal resolution of the microscope.

Faster and more expensive optical detectors may be employed to address this problem, but signal processing circuitry used to analyze the optical detector output must also be responsive on an equally fine temporal resolution thereby complicating this circuitry. For instance, a microchannel plate detector used as an optical detector has a frequency bandwidth of up to approximately 10 GHz. Even this frequency fails to take advantage of commonly available excitation laser systems which operate at frequencies of up to approximately 220 GHz. The signal processing circuitry used to isolate phase and modulation information from the responsive fluorescence signal must operate at a frequency corresponding to that of the optical detector, providing additional difficulties in implementation even when an ultrafast detector is used.

Reduction of signal frequency viewed by the signal processor may be accomplished by mixing a cross correlation frequency with the modulated photocurrent of the fluorescence from the optical detector in a microscope excited by a sinusoidally modulated laser. The combined signal has a frequency equal to the difference between the cross correlation signal and the optical sensor photocurrent, which requires less temporal resolution in the signal processing circuitry. Nonetheless, the temporal resolution of the optical detector will set the maximum frequency of fluorescence phenomena from which information concerning individual fluorescence lifetimes may be obtained.

Pump probe excitation techniques have been proposed outside of microscopy, for instance in spectroscopy. One approach proposed by Elzinga et al., includes the use of offset pump and probe repetition frequencies. *Pump/Probe method for fast analysis of visible spectral signatures utilizing asynchronous optical sampling*, Applied Optics, vol 26, no. 19, p. 4303 (October 1987). Spectral signatures are analyzed by looking at intensity information from an obtained cross correlation signal. According to Elzinga's spectroscopic system temporal information of the sample is obtained by recording the intensity of the difference frequency as a trigger, and the entire decay process is examined. Such an approach is inapplicable to microscopy because image acquisition times would be unreasonable.

Accordingly, it is an object of the present invention to provide a fluorescence microscope which provides improved spatial and temporal resolution.

A further object of the present invention is to provide a frequency domain fluorescence microscope having a temporal resolution greater than that of an optical sensor used in the microscope.

Another object of the present invention is to provide a scanning fluorescence frequency domain microscope having picosecond temporal resolution and three dimensional spatial resolution while using a full field optical detector of less than picosecond temporal resolution.

An additional object of the present invention is to provide a scanning fluorescence frequency domain microscope in which two modulated excitation lasers of different frequencies are combined and overlapped onto a sample to stimulate a low frequency cross correlation optical fluorescence emission from the sample from which phase and modulation information may be obtained.

Still another object of the present invention is to provide a fluorescence frequency domain microscope with offset pump and probe repetition frequencies, and which obtains image data from a low frequency cross correlation optical fluorescence emission with low harmonic noise and with a pixel acquisition rate which makes image obtainment practicable, A still further object of the present invention is to provide a fluorescence frequency domain microscope with offset pump and probe repetition frequencies, and which obtains image data from a Fourier transformed sample of a cross correlation fluorescence signal emitted from the sample, using a sampling frequency which permits acquisition of an image frame in a short time period.

SUMMARY OF THE INVENTION

The above-listed objects are met or exceeded by the present frequency domain cross correlation pump probe fluorescence microscope. A microscope in accordance with the present invention includes a first modulated laser of a first frequency, and a second modulated laser of a second frequency. Preferably, the difference between the first and second frequencies is small, but may be set arbitrarily to conform to an acceptable frequency for detection circuitry in the microscope. The beams output by the two lasers are combined and focused upon an autofluorescent or stained sample in a spatially overlapped fashion. Optics used to combine and focus the beam may include scanning mirrors to perform a raster scan of the focused combined beam upon the sample in accordance with standard video formatting techniques. In response to the excitation of the combined excitation beam, the sample emits fluorescence including a cross correlation signal having a frequency equal to the difference between the emission frequencies of the first and second excitation lasers. A detector used to sense the responsive fluorescence need only have a temporal resolution to sense the low frequency cross correlation signal. Output of the sensor is digitized, sampled, and Fourier transformed and image data is obtained from either or both of the phase and modulation of the Fourier transformed sampled signal.

Preferably, the sampling rate is chosen to produce image frame acquisition rates of a few seconds, while permitting sufficient information to be obtained to eliminate harmonic distortion.

According to the illustrated embodiment of the present invention, efficient high-resolution fluorescence lifetime imaging of samples is realized. Additional preferred embodiments of the present invention include a microscope in which the polarization of the pump beam relative to the probe bream is varied to permit measurement of polarization relaxation of excited state molecules.

While pulse modulated Nd-YAG lasers are used to realize the pump and probe lasers of the present invention, a sinusoidally modulated stable diode laser implementation is also contemplated. A microscope constructed in accordance with the present invention may also conduct three dimensional sectioning of thick samples through adjustment of the relative distance between an objective lens used to focus the combined excitation beams upon the sample.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

Other features, advantages and objects of the invention will be readily apparent to those skilled in the art by reference to the detailed description and drawings, of which:

FIG. 1b is a block diagram of a signal processing and control system of the data acquisition computer of FIG. 1a;

FIG. 6a–6d are amplitude and phase image of human red blood cells and mouse fibroblast cells from the microscope system of the present invention and from a standard one-photon fluorescence microscope;

DETAILED DESCRIPTION OF THE PREFERRED EMBODIMENT

Figure 1A:
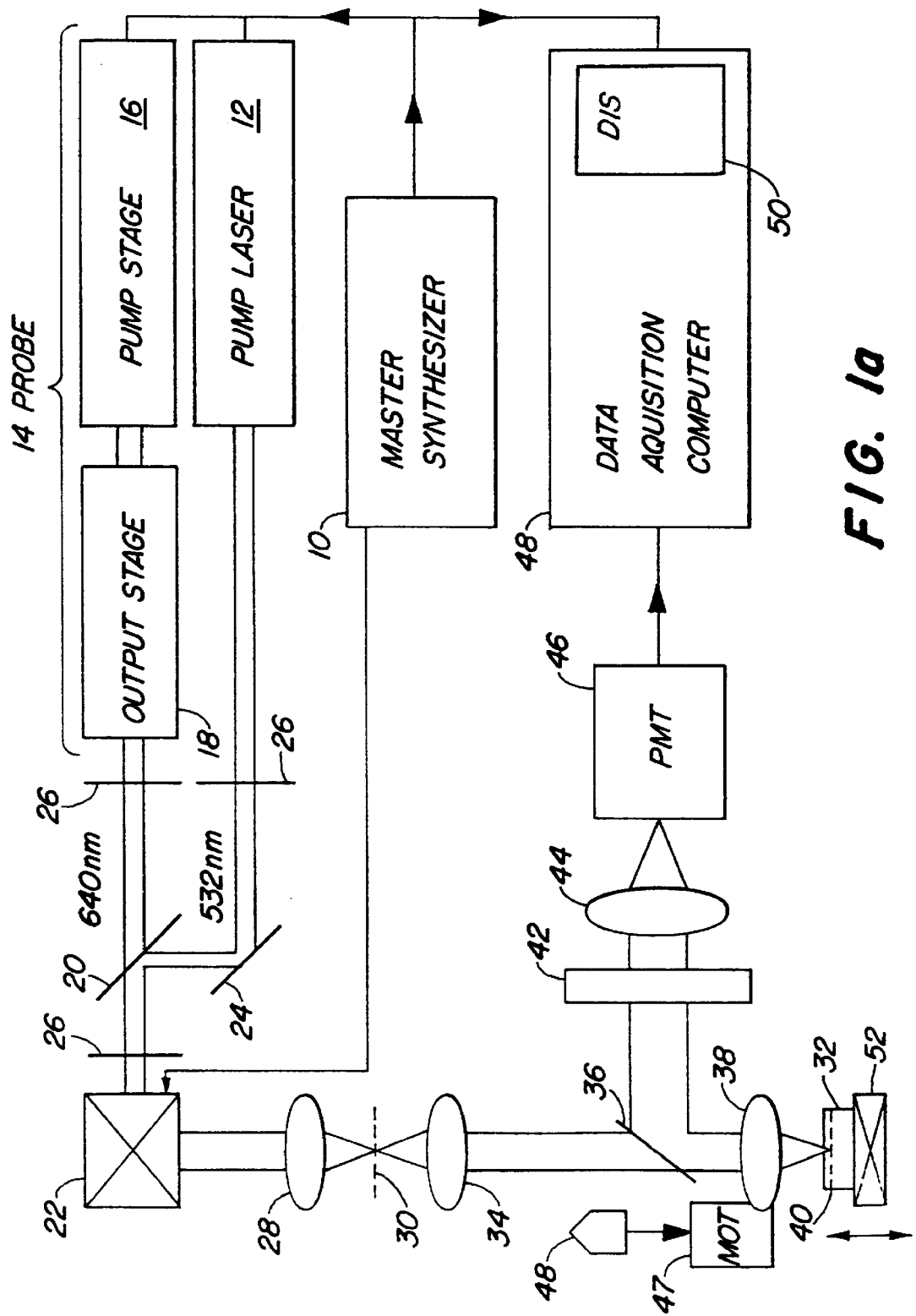
FIG. 1a is block diagram of a scanning fluorescence microscope constructed in accordance with the present invention.

Referring now to FIG. 1a shown is an embodiment of a frequency domain scanning fluorescence microscope in accordance with the present invention. A master synthesizer 10 generates a reference oscillation signal, for instance of 10 MHz, which is used to phase lock pump 12 and probe 14 excitation lasers. In the illustrated embodiment the probe laser 14 is constructed in separate pump 16 and output 18 stages. Both the pump stage 16 and 18 may be realized by commonly available mode-locked neodymium-YAG lasers. The output of the pump laser 12 is used directly, while the pump stage 16 of the probe laser 14 drives the output stage 18. A suitable output stage laser is a DCM dye laser.

A more compact and lower cost system may be realized through implementation of the pump 12 and probe lasers 14 using sinusoidally modulated diode lasers. Typically available diode lasers are generally not sinusoidally modulated. However, such modulation is realizable through a combination of DC and AC drivers for the lasers. The DC driver supplies a sufficient threshold current to turn on the lasers, and the AC driver is responsible for supplying a sinusoidal current into the lasers to driver their intensity accordingly. Generally, the diode lasers are more compact, inexpensive and stable, providing for an efficient pumping and probing mechanism in a microscope constructed according to the present invention.

To achieve time resolved fluorescence microscopy in accordance with the present invention, the pump 12 and probe 14 lasers are set to sinusoidally modulate at slightly different frequencies. The particular difference frequency between the two lasers should be set in accordance with the detection and signal processing hardware in a given construction of the present microscope invention. This difference frequency should not exceed the temporal resolution of either the detection or processing hardware. Excepting that condition, the difference frequency may be chosen arbitrarily to suit a particular application. A factor to consider in choosing the difference in frequencies is avoidance of noisy spectral regions. The eventually detected signal will be an integral multiple of the difference frequency. Smaller differences in frequencies should be chosen to observe faster fluorescence lifetime decays.

The pump and probe beams are overlapped at the focus point on the sample, as illustrated in FIG. 1a. Their wavelengths are chosen such that one beam (pump) is used to excite the molecules under study and another beam (probe) is used to stimulate emission from the excited state chromophores. The two pulse trains are offset in frequency by a small amount. This arrangement generates a fluorescence signal at the cross correlation frequency and corresponding harmonics. Since the cross correlation signal depends strongly on the efficient overlap of the two laser sources, superior spatial resolution can be obtained by detecting the fluorescence at the beat frequency or its harmonics. Furthermore, the low-frequency, cross correlation signal contains the response of the chromophores to high laser frequency harmonics.

An exemplary embodiment of the present invention set the pump laser 12 at 76.2 MHz+2.5 KHz, and the probe laser 14 at 76.2 MHz–2.5 KHz, resulting in respective output wavelengths of 532 and 640 nm, and pulse widths (FWHM) of 150 and 10 ps. The difference (cross correlation) frequency is therefore a relatively small 5 KHz, which is low enough to sense and analyze without difficulty. Ordinary photomultipliers are capable of detecting frequencies of up to 10 KHz, so if the difference frequency is chosen in this range, the optical detection portion of the microscope system will not limit the temporal resolution of the overall system. However, the phase relationship of the separate lasers must be stable to enable use of the high harmonic content of the pulses. Separate phase locked high resolution frequency synthesizers will adequately drive mode locking of the pump 12 and probe 14 lasers. Phase drift is undesirable since it limits ability to exploit high harmonic content of the beam pulses. Wavelengths of the lasers are chosen so that the pump laser beam excites chromophores being studied, while the probe beam induces stimulated emission.

Additional time-resolved spectral information can be obtained by varying the wavelengths of either the pump or the probe beams. The photons of the pump beam at a fixed spectral wavelength have a definite energy. These excitation photons will excite the molecule to particular energy levels of the excited state. By inputting the second probe beam at a time which is short (on the order of femtoseconds) as compared to the energetic relaxation of the excited state molecules, it is possible to selectively depopulate a band of the excited state spectrum which has energy matching the probe beam photon energy. This is the excited state hole burning effect. Using different pump or probe beam wavelength (energy) and monitoring the remaining fluorescence as a function of time, observation of the dynamics of the re-population of the different depleted region in the excited state energy spectrum is observed.

Similarly, according to an additional embodiment of the present invention, time-resolved polarization information is obtained by varying the polarization of either the pump or probe beams. For example, the pump laser 12 may be set at a predefined polarization to prepare an excited state to a pure polarization state, while the probe laser 14 is set at a different polarization state. With the different polarization states, the excited state is transparent to the probe laser 14, e.g. no interaction occurs, on a time scale which is short compared to the molecular relaxation time. By allowing the molecules to relax on a longer time scale (femtoseconds to picoseconds) the excited state will not be a pure polarization state due to molecular rotational relaxation. In this case stimulated emission caused by the interaction of the probe beam with a portion of the excited state which has an emission dipole parallel to the probe beam polarization will be observed. Observation of the stimulated emission effect over time allows measurement of polarization relaxation of excited state molecules when the polarization of the pump and probe beams is varied.

A dichroic mirror 20 combines output beams from the pump 12, directed by mirror 24, and probe lasers 14, and directs the same to a scanner 22. Polarizers 26 serve to control laser power in the pump, probe and combined beams. The polarizers 26 immediately adjacent the pump 12 and probe lasers 14 may be used to vary the polarization to observe the polarization relaxation.

The scanner is synchronized from the reference frequency provided by the master synthesizer 10, and produces a scan pattern suitable for an output image format. Scanning mirrors (unshown) within the scanner may be driven through an analog or digital signal. For an image composed of 256×256 pixels, X and Y scanning mirrors are set to a range of ±60 degrees, with each angular position being specified by a 16 bit binary number.

Upon exit from the scanner, the combined beam enters a scan lens 28, positioned so that the x-y scanner is at the eye-point of the scan lens 28 while the field aperture plane is at its focal point. The scan lens linearly transforms the angular deviation of the combined beam output from the x-y scanner to a lateral translation of the focal point position at the field aperture plane 30. From the scan lens 28, the combined beam enters what may be a generally standard microscope focal system. Such combination allows the present invention to be practiced as an addition to existing microscope systems.

The optical microscope portion used in accordance with the present invention must focus the scanned combined beam upon a sample 32, and detect responsive fluorescence emissions from the sample 32. From the scan lens 28, the beam is collimated by collimating lens 34, and passed through a dichroic mirror 36. An objective lens 38 spot focuses the beam upon the sample 32. Since the field aperture plane is telecentric with respect to the object plane 40 of the sample 32, movement of the focal point on the object plane 40 is proportional to the angular deviation of the scanned combined beam.

The objective lens 38 should be well corrected and have a high numerical aperture to produce a tight focus. A 63x objective having a numerical aperture of 1.25 is suitable. Tight focusing increases photon density and accordingly enhances the obtained pump-probe effect.

Responsive fluorescence is passed through the objective lens 38, and is transmitted by the dichroic mirror 36 through a filter 42. In the illustrated embodiment, the filter 42 is constructed of two 600±20 nm bandpass filters. A collection lens 44 refocuses the emitted fluorescence into a photomultiplier tube 42, or other suitable detector.

Three dimension sectioning is created by relative movement between the objective lens 38 and the sample 32. A stepping motor 47 effects vertical movement of a vertical adjustment mechanism of the objective lens 38 under control of a linear variable differential transformer 52. In the illustrated embodiment, the control system is designed to have a position resolution of 0.2 µm over a total range of 200 µm. Once a complete raster scan has been executed by the scanner 22, the depth of the focal plane 40 within the sample is adjusted under control of a data acquisition computer.

Figure 1B:
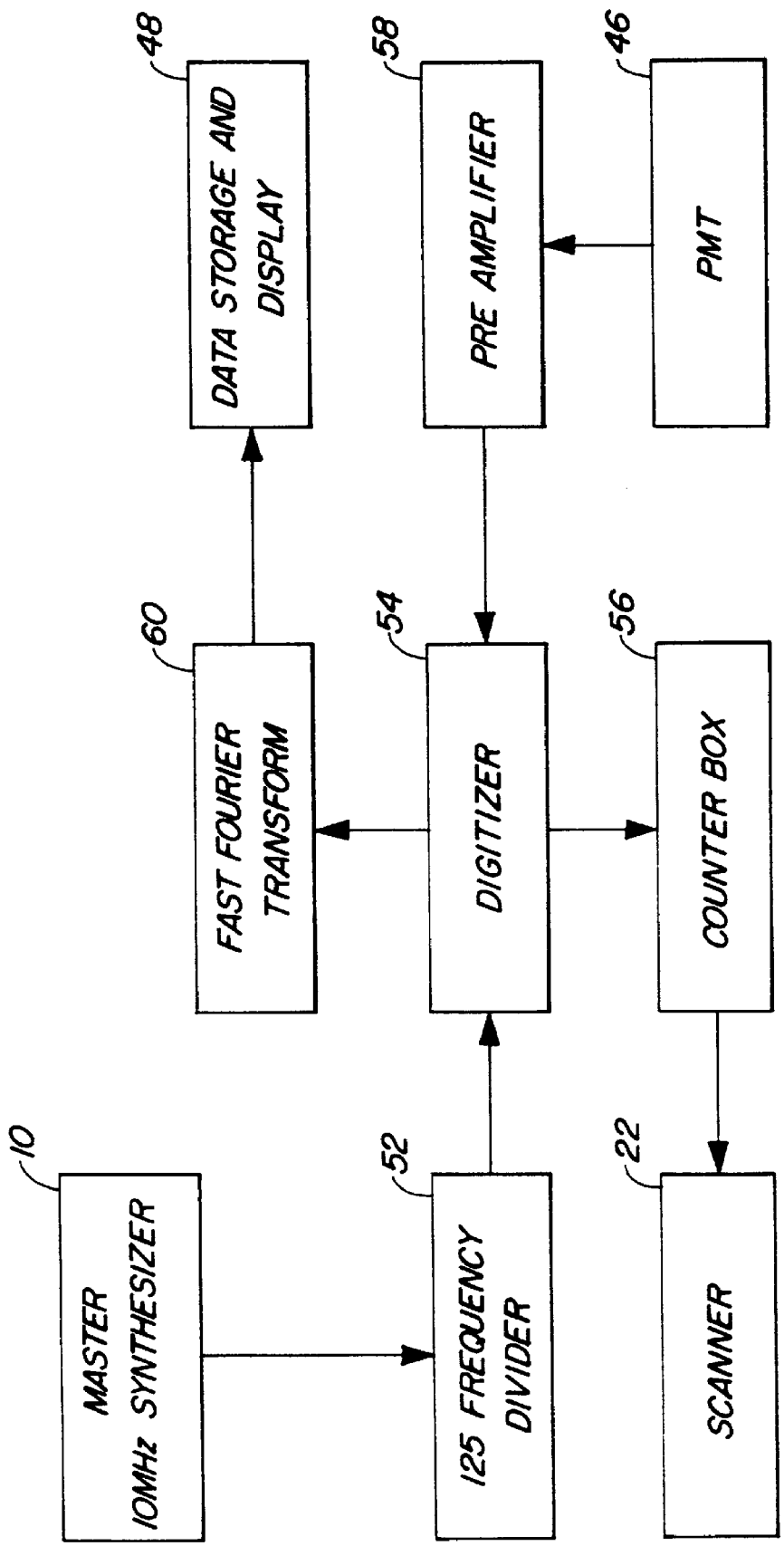
Figure 2:
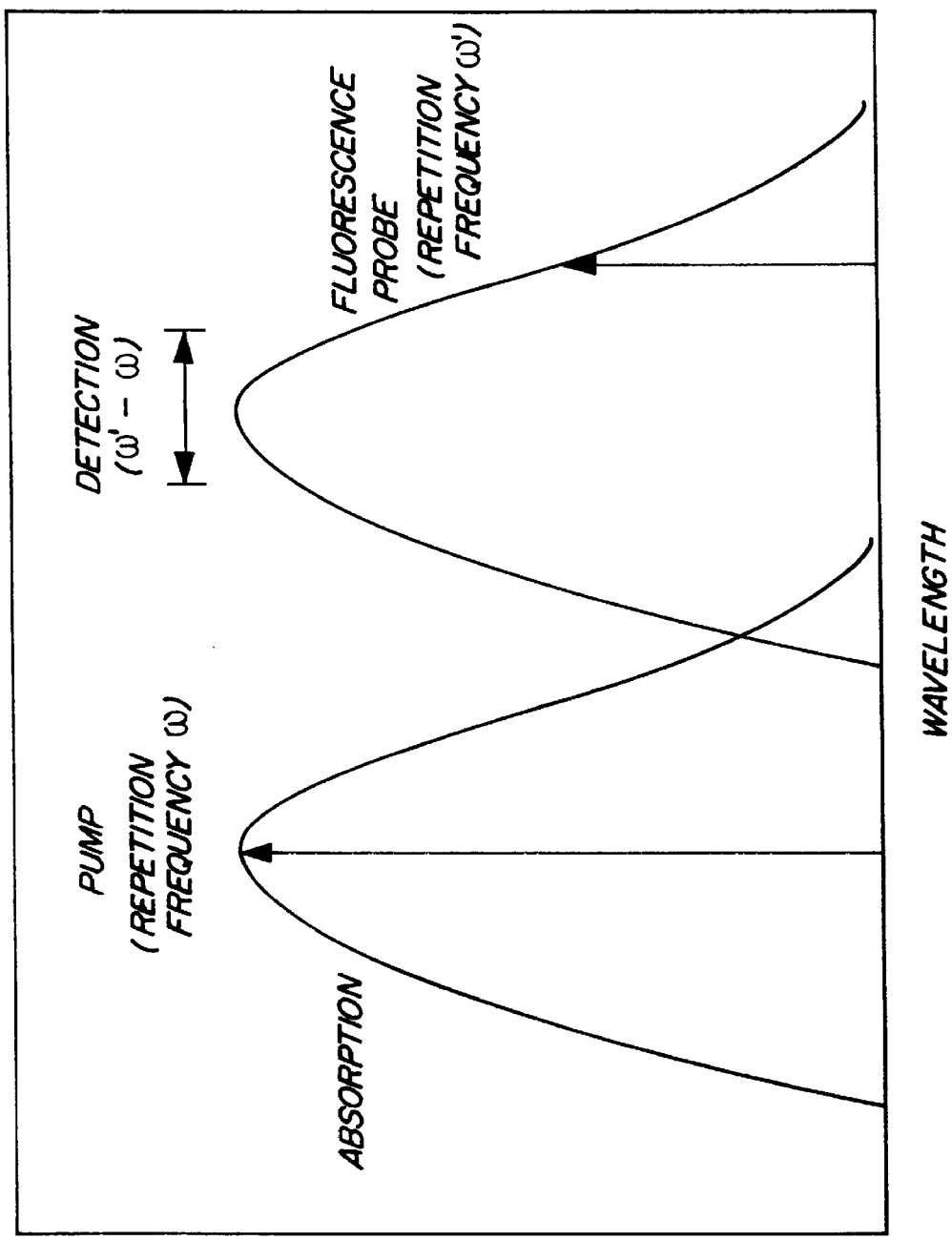
FIG. 2 illustrates a spatial overlap principle of the pump and probe beams.

A data acquisition computer 48, which may be a personal computer or a special purpose computer, including a display 50 is used to analyze the data from the photomultiplier 46, and control system operation. Referring now the FIG. 1b, shown is a block diagram illustrating the control and data acquisition functions, realizable through firmware or software, of the data acquisition computer 48 and associated microscope components from FIG.1a.

The master synthesizer 10 provides the system synchronization pulse, for instance of 10 MHz, to a frequency divider 52, dividing the signal to 400 KHz. A digitizer 54 provides instructions for a counter 56 to move from pixel to pixel via one line, and instruction to reset the counter 56 upon completion of a full scan of one frame. The counter box outputs the x, y coordinates in digital form to the scanner 22. A suitable commercial scanner is a Cambridge Technology Scanner System. The counter 56 also generates appropriate x-strobe and y-strobe signals to drive the scanner 22 so that the x and y coordinates are identifiable in the digital numbers sent from the counter 56. The digital positions obtained from the count and strobe are used to galvo-drive a pair of scanner mirrors (not shown) in the scanner 22, whose movements translate to deviation of the combined beams onto the sample 32.

The analog signal from the PMT 46 is electronically filtered by a pre-amplifier 58 to isolate the 5 KHz, cross-correlation signal. The filtered signal is then digitized by the digitizer 54, which is a 120 KHz, 12-bit sampling digitizer in the illustrated embodiment. The Shannon Sampling Theorem dictates that at least two points per waveform need to be acquired to determine a sinusoidal signal. However, the signal can be significantly distorted by higher order harmonics if only the minimum two points are used. Preferably, at least four points per waveform are acquired to reduce harmonic noise. Digitization of four points per waveform eliminates all odd harmonic distortion and also eliminates even harmonics up to the eighth order. Of course, more accurate signal and more detailed temporal information may be obtained by digitizing more points per waveform, but it is rarely desirable for imaging applications. According to the present invention, the pixel residence time must be sufficiently short to obtain a reasonable frame acquisition rate. In determining the number of sampling points the following relationship between the cross correlation frequency ($\Delta f$), the maximum digitizer rate ($f_d$) and the number of sampling points per waveform should be considered:

$$\Delta f = \frac{f_d}{n}$$

Thus, increasing the number of points digitizes lowers the possible cross correlation frequency which may be examined. As an example, using a fast high resolution (12 to 16 bit) digitizer with a digitization rate of 100 KHz, digitization of four points per waveform sets a limit of about 25 KHz for the cross correlation signal, resulting in a reasonable frame rate of approximately 3 seconds for a 256×256 pixel image. If an increase is made to 64 points per waveform, the frame rate quickly increases to approximately 50 seconds.

After sampling in the digitizer 54, the cross correlation signal is sent to a fast Fourier transformer 60. The data acquisition computer 48 obtains intensity, modulation and phase data from the transformed sampled cross correlation signal, where the data may be stored and displayed. Fluorescence lifetime is obtained from the transformed sampled cross correlation signal because the movement of the scanner and the generated cross correlation signal are synchronous to the master synthesizer 10.

The generation of a low frequency cross-correlation signal which impinges on the PMT 46, and analysis in the frequency domain in accordance with the present invention, provides improved spatial resolution and time-resolved, high frequency information, as demonstrated by consideration of a species of molecule decays exponentially under sinusoidal excitation as described by Eqn. (1)–(3). Since stimulated emission propagates in the same direction as the radiation inducing such transition, the modulated probe beam with intensity profile $I'(\vec{r},t)=I'(\vec{r})I'(t)=I'(\vec{r})(1+m'_e \sin(\omega't+\phi'))$ causes a decrease in fluorescence collected by the objective lens 38 used in focusing and overlapping the two lasers 12 and 14. The observed fluorescence $$F_{obs}(t)=F(t)-\Delta F(t) \quad (4)$$

changes by an amount proportional to the overlapping integral of the pump 12 and the probe 14 beam profiles $$\Delta F(t) \alpha c \sigma \sigma' q(1+m_e \sin(\omega't+\phi'))(1+m_f \sin(\omega t+\phi))\int I(\vec{r})I'(\vec{r})d^3r \quad (5)$$

where $\sigma$ is the stimulated emission cross-section. The product term $I(t)I(t')$ in Eqn. (5) may be rewritten as the combination of two terms containing sum and difference of frequencies $\omega$ and $\omega'$. As a result, Eqn. (4) contains a cross-correlation term at the difference of the pump and probe beam repetition frequencies $|\omega'-\omega|$, $$\Delta F_{cc}(t) \alpha c \, \sigma\sigma' q m_f m'_e \cos[|\omega'-\omega|t+(\phi'-\phi)]\int I(\vec{r})I'(\vec{r})d^3r \quad (6)$$

The component of the fluorescence signal containing the cross-correlation signal is detected. As a result, lifetime of the chromophore can be determined from its phase and modulation.

The effective spatial resolution in the microscopic imaging system of the present invention depends on the focusing of the combined pump-probe beam and detection of the responsive fluorescence signal. In a conventional fluorescence microscope, the intensity distribution near the focal point of a circular objective with numerical aperture NA is given by $$I(u,v)=|2\int_0^1 J_0(vp)e^{1/2\, iup^2}p\,dp|^2 \quad (7)$$

where $$u=\frac{2\pi}{\lambda}(NA)^2 z \text{ and } v=\frac{2\pi}{\lambda}(NA)r$$

r are the dimensionless optical coordinates in the axial and radial dimension respectively, and $\lambda$ is the wavelength of light focused. In a pump-probe fluorescence microscope according to the present invention in which both the pump and probe processes involve a one-photon transition, the strength of the cross-correlation signal described in Eqn. (6) is proportional to the spatial integral of the intensity product of the pump and probe sources $$\int I(u',v')I'(u',v')d^3t, \quad (8)$$

where the pump and probe intensity distribution is represented by the unprimed and primed coordinates respectively. Eqn. (8) shows that the pump-probe point spread function (psf)I(u,v)I'(u',v') is mathematically similar to the psf of two-photon excitation microscopy $I(u,v)^2$, but at roughly half the wavelength. This results in improved spatial resolution from 22 conventional one-photon and two-photon excitation microscopy. Furthermore, the pump-probe psf is identical to that for confocal microscopy if the stimulated emission wavelength is the same as the confocal detection wavelength. Thus, one-photon pump-probe microscopy of the present invention provides comparable spatial resolution as confocal microscopy but without confocal detection, and the associated mechanical complexities.

High Frequency Testing of Microscope System

High frequency performance of the microscope system of the present invention was tested by use of a sample of Rhodamine B in water. The pump laser 12 was operated at 76.2 MHz and the probe 14 laser's repetition frequency was 76.2 MHz+210 Hz. To enhance the signal to noise ratio at higher cross-correlation harmonics, the pump 12 laser power was increased to 48 $\mu$W and the probe 14 laser power was increased to 3 mW. The fluorescence signal was collected and optically filtered in the same manner as for imaging, and the photomultiplier signal was fed directly into a spectrum analyzer where the harmonics were displayed and stored.

1. Pump-Probe Signal Dependence on Laser Power Level

As the pump or probe laser power is increased, eventually the signal will saturate due to the depletion of chromophores in the focal volume available for the pump-probe process. Off-focal signal can begin to contribute significantly resulting in broadening of the point spread function and deterioration of the spatial resolution.

Figure 3A:
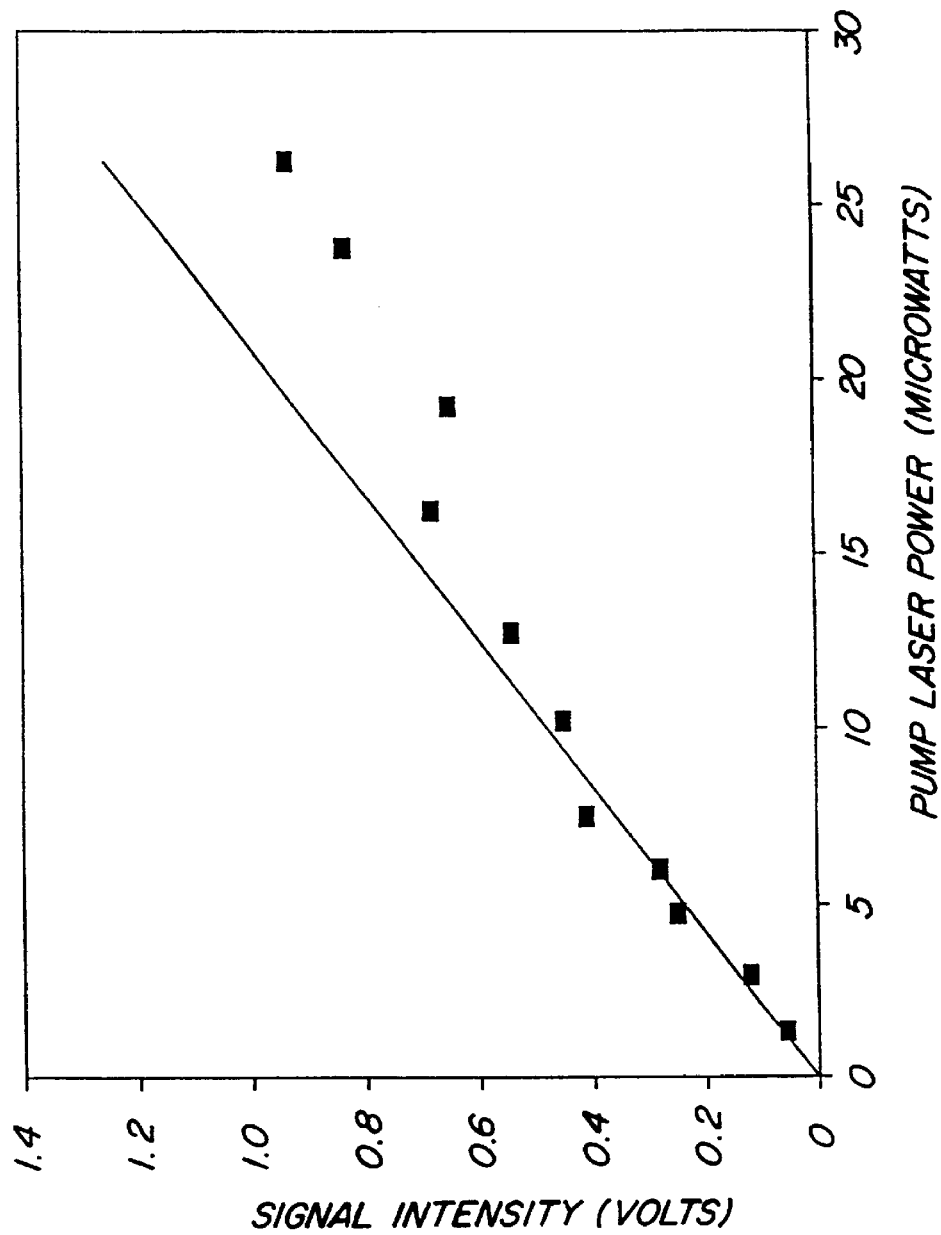
FIG. 3a is a plot of output fluorescence versus pump laser power.
Figure 3B:
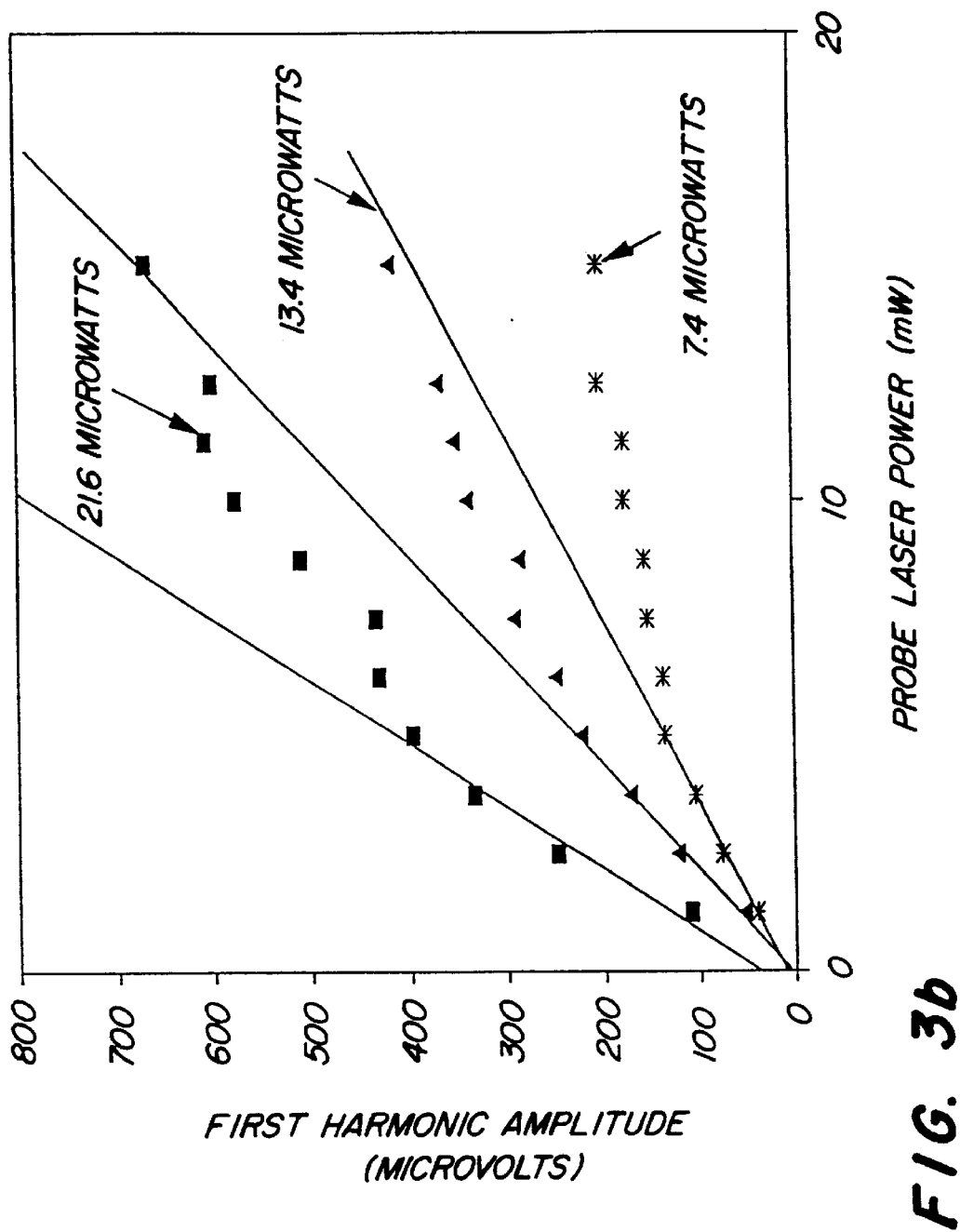
FIG. 3b is a plot of calibration curves for probe laser power.

For a linearity test, aqueous Rhodamine B (7.8 mM) sealed (with nail polish) between the coverslip and a microscope slide was used. The test was performed in two steps. First, the pump laser 12 is focused onto the Rhodamine B sample and the PMT output induced by the fluorescence is measured as a function of the pump laser power. The result is shown in FIG. 3a where the effect of saturation is evident starting at about 12.8 $\mu$W. Next, the probe laser 14 is also focused onto the Rhodamine B sample. At three different pump laser settings of 2.37, 4.29, and 6.91 $\mu$W, the first harmonic amplitude of 5 KHz is recorded as a function of the probe laser's power. The three calibration curves are plotted in FIG. 3b along with best linear fits using the first five points of each data set. The figure shows that saturation of the first harmonic amplitude begins at about 1.5 mW.

In Table 1, the ratio of the pump power and slope relative to the pump power of 7.4 $\mu$W are compared.

TABLE 1

Ratio of Relative Pump Power and Slope of Probe Curve

| Pump Power (Microwatts) | 2.37 | 4.29 | 6.91 |
|---|---|---|---|
| Pump Power/2.37 | 1 | 1.81 | 2.92 |
| Slope/Slope 2.37 | 1 | 1.76 | 2.95 |

Results in Table 1 shows that the ratio of relative slope agree well with the relative pump power (3% for 13.4 $\mu$W and 1% for 21.6 $\mu$W). Thus for Rhodamine B in water, 12.8 $\mu$W and 1.4 mW are the limits for signal linearity for pump and probe beams, respectively. These values also represent the upper limits in power levels used in prototype testing. Note that the power saturation level for the probe laser 14 is roughly two orders of magnitude higher than that for the pump laser 12. The difference in power may be attributed to several factors. First the absorption and stimulated emission cross-sections may be quite different at the wavelengths chosen. For Rhodamine 6G, a closely related species of Rhodamine B., the absorption at (532 nm) and stimulated emissions (at 640 nm) are about $2.6 \times 10^{-16}$ cm$^2$ and $4.0 \times 10^{-17}$ cm$^2$ respectively. As a result, the difference in cross-sections can contribute to an order of magnitude higher probe laser power needed in observing saturation effects. Other factors such as pump and probe beam overlapping efficiency, excited state molecules rotational effect, and Rhodamine B's quantum efficiency can contribute to the fact that higher probe laser power was needed to observe saturation effects in the cross-correlation signal.

The calibration data above is only valid for Rhodamine B in water at the wavelengths chosen. The estimation of the power for pump laser saturation may be extended to other chromophores if their extinction coefficients are known. To estimate the probe beam saturation power for other chromophores, their cross-sections relative to that of Rhodamine B in water need to be determined. Where the chromophores' spectroscopic properties are not always known, the power level chosen for their studies remained to be 12.8 $\mu$W for the pump beam and 1.5 $\mu$mW for the probe beam, both are below the saturation points for Rhodamine B in water. Upon measurement of emission cross-sections of some common chromophores, the absorption, quantum efficiency, and stimulated emission data can then be useful in assessing the laser saturation levels for each species of chromophores.

2. Point Spread Function and Axial Depth Discrimination

Figure 4:
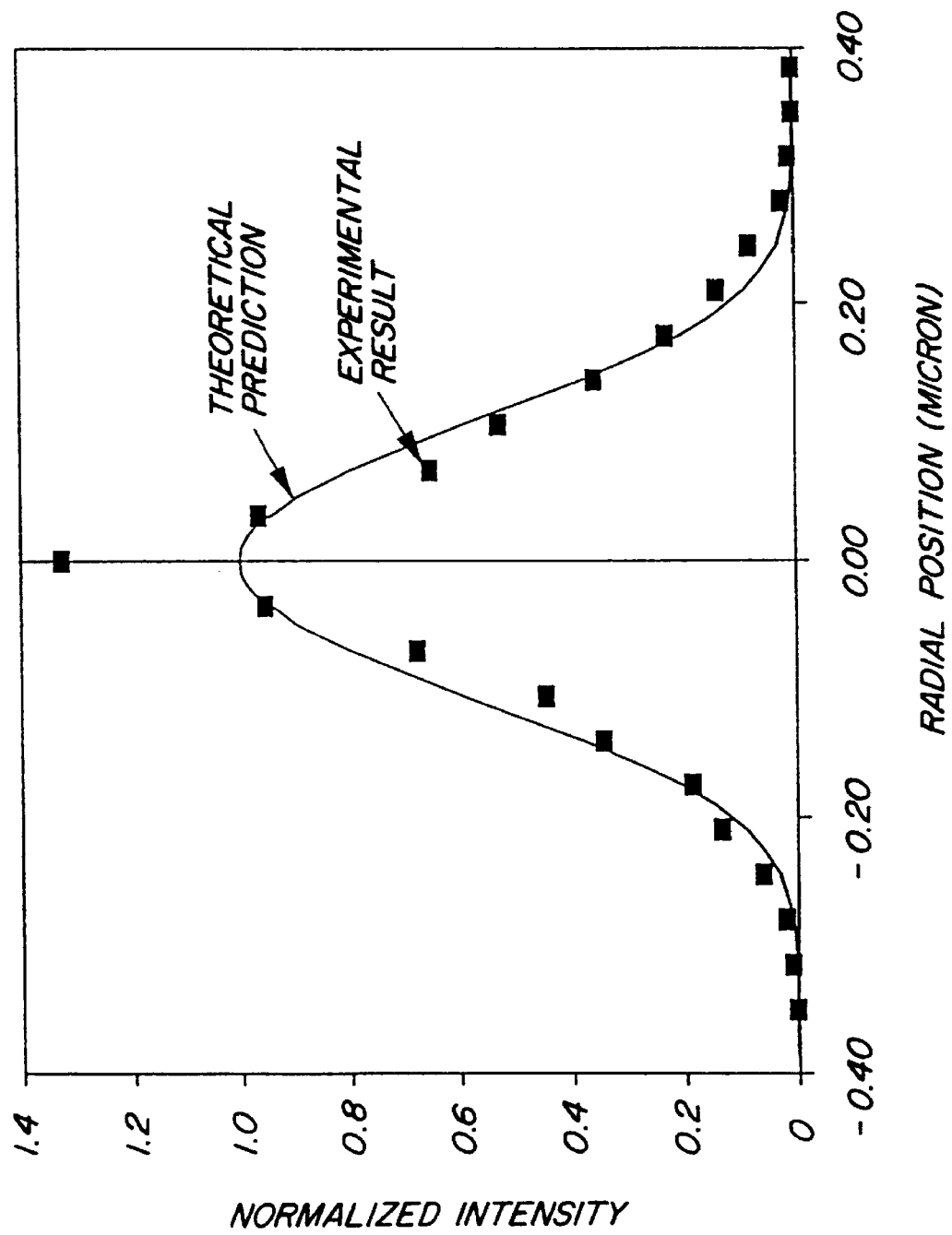
FIG. 4 is a normalized intensity plot of orange latex spheres imaged with the microscope of the present invention.

The spatial resolution of the microscope is determined by its point spread function (psf). To characterize the radial and acial spatial resolution of the system, orange fluorescent latex spheres of 0.28 $\mu$m in diameter (absorption maximum: 530 nm, emission maximum: 560 nm; Molecular Probes, Eugene, OR) were immobilized between a cover slip and a flat microscope slide with Fluoromount G. mounting medium, (Souther Biotechnology, Birmingham, Ala). The slide was left to dry at room temperature for one day before the spheres were imaged inside the microscope. The size of these latex spheres was uniform and calibrated by the manufacturer using electron microcopy. Since the size of the spheres is comparable to the FWHM of the theoretical psf at the pump and probe wavelengths, the fluorescence intensity measured needs to be compared to the intensity distribution from convolution of the theoretical psf to the sphere size. The radial and axial profiles were normalized and averaged for data from 36 spheres. The intensity profiles are shown in FIG. 4 along with normalized theoretical profiles, in axial coordinate z and radial coordinate r, given by $$I_{sphere}(z, r) = \frac{I(z, r)I'(z, r) \otimes S(z, r)}{I(0, 0)I'(0, 0) \otimes S(0, 0)} \quad (9)$$

where S(z,r) characterizes the physical dimension of the spheres and it is 1 for $\sqrt{z^2+r^2} \leq 0.14$ $\mu$m and 0 otherwise. As the figure shows, the experimental and theoretical intensity profiles agree well each other.

3. Applications to Time-Resolved Imaging a. Imaging of Fluorescent Latex Spheres.

Figure 5A:
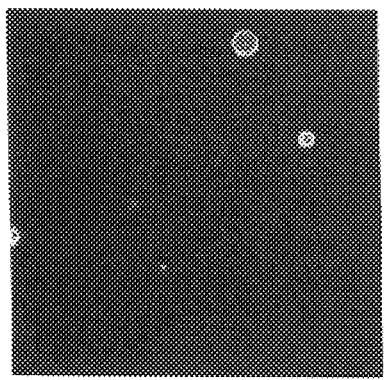
FIG. 5a is a plot of first harmonic amplitude and FIG. 5b the phase information for orange and red latex spheres imaged with the microscope of the present invention.
Figure 5B:
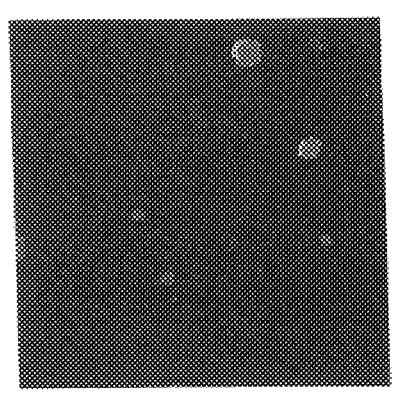
Figure 6A:
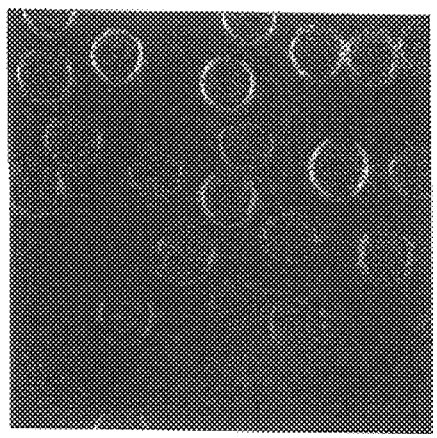
Figure 6A:
Figure 6B:
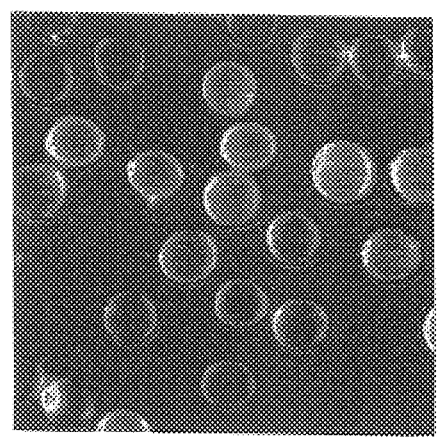
Figure 6B:
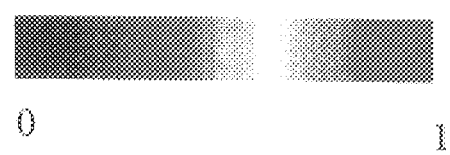

First harmonic amplitude and sphere information are shown in FIG. 5, for a mixture of 2.3 $\mu$m orange and 1.09 $\mu$m Nile-red (absorption maximum: 520 nm, emission maximum: 580 nm) fluorescent latex spheres (Molecular Probes, Eugene, Oreg.). The measured phase values are referenced to that of a Rhodamine B slide for the purpose of lifetime calculations. The histograms of lifetime values in the spheres gave an average lifetime of 3.33±0.98 ns for 1.09 $\mu$m spheres and 4.35±1.48 ns for 2.3 $\mu$m spheres. The error is the standard deviation from the histogram of lifetime values. For comparison, the lifetimes of the spheres were separately determined inside a cuevette by standard frequency-domain phase fluorometry. The lifetimes determined in this manner are 2.70 ns for 1.09 $\mu$m spheres and 4.28 ns for 2.3 $\mu$m spheres. The value for both sphere size agrees within error by the two methods. Lifetime imaging in accordance with the present invention thus provides a way to image different chromophores with similar emission spectra but different lifetimes.

b. Comparison Between Conventional Microscopy and Pump-Probe Fluorescence Microscopy in Human Erythrocytes and Mouse Fibroblast.

To demonstrate the superior spatial resolution achieved by pump-probe fluorescence microscopy in accordance with the present invention compared to conventional one-photon microscopy, two commonly used biological systems were imaged: human erythrocytes and mouse fibroblast cells.

The human erythrocytes were labeled with the membrane dye Rhodamine DHPE (Molecular Probes, Eugene, Oreg. A small amount of erythrocytes was mixed with Hanks Balanced Salt Buffer (HBSB with NaHCO$_3$) to make a 1 mL mixture. The solution was spun at 1000 rpm for 5 minutes before the top buffer was removed. The erythrocytes were then shaken and diluted to 1 mL with HBSB. 6 $\mu$L of Rhodamine DHPE (at 5 mg/mL DMSO) was injected into the solution containing the cells and allowed to incubate for 30 minutes. After incubation, the cells were again spinned down and washed with HBSB two more times to remove residual dye before mounting onto a well microscope slide. Nail polish was used to seal the coverslip.

The mouse fibroblast cells were grown on a coverslip. For fixation, they were placed in acetone for 5 minutes and allowed to air dry. Then, a few drops of a solution containing 10 $\mu$g/mL of Rhodamine DHPE (diluted in PBS, 0.1% Triton X-100) were placed onto the coverslip and incubated for 30 minutes. After incubation, the dye was removed by rinsing the coverslip in PBS buffer twice before mounting onto a flat microscope slide. For mounting, a drop of the mounting medium Prolong (Molecular Probes, Eugene, Oreg.) was placed between the coverslip and a slide. In a few hours, the mounting medium dries and the slide was ready for viewing.

The image at the first harmonic of 5 KHz is presented in FIGS. 6a–6d long with the corresponding one-photon images. The one-photon images were obtained by blocking the probe beam and by recording only the fluorescence intensity due to the pump beam. In this manner, the cells were not moved relative to the microscope objective and a comparison between the two techniques can be made. From the erythrocytes'image, it is apparent that the pump-probe images can better reject the fluorescence from off-focal planes. The one-photon images shows much more background fluorescence from the central region of the erythrocytes than pump-probe microscopy. Similarly, the pump-probe image of the mouse fibroblast also shows superior spatial resolution compared to the corresponding one-photon image. The finer details revealed are the evidence of superior spatial resolution and of the off-focal fluorescence rejection.

c. Multiple Dye Labeled Mouse Fibroblast.

Figure 7A:
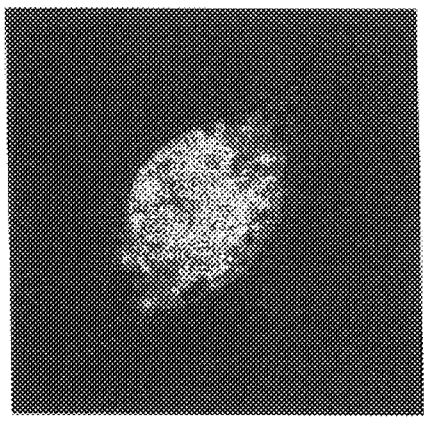
FIG. 7a shows the first harmonic amplitude and FIG. 7b the phase for a multiple dye labelled mouse fibroblast cell imaged in accordance with the present invention.
Figure 7A:
Figure 7B:
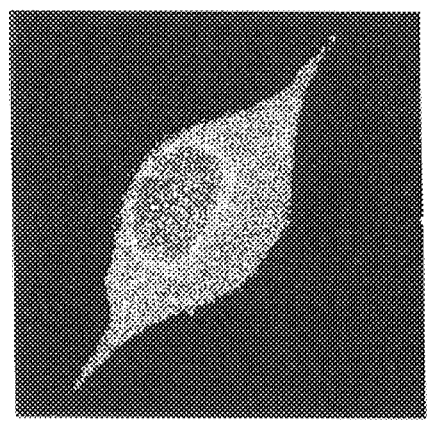
Figure 7B:
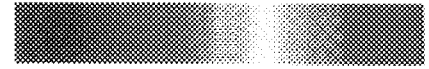

Mouse fibroblast cells doubly labeled with the nucleic acid stain ethidium bromide and with the membrane stain Rhodamine DHPE (Molecular Probes, Eugene, Oreg.) were also imaged. The pump-probe image is shown in FIGS. 7a and 7b. These cells (grown on a coverslip) are fixed and stained in the same manner as the mouse fibroblast cell discussed above. The only difference is that the coverslip was covered first with ethidium bromide (1 mM in PBS, 0.1% Triton X-100) for 30 minutes and then stained by Rhodamine DHPE (10 $\mu$/mL in PBS, 0.1% Triton X-100) for another 30 minutes before it was rinsed twice in PBS and mounted for viewing. The lifetimes of the cytoplasmic and nuclear region were determined from the phase image. The reference phase was obtained from a slide of 7.8 mM Rhodamine B in water. It was found that the average of lifetime histograms in the cytoplasm and nucleus are 2.08±0.55 ns and 6.88±4.96 ns, respectively. For comparison, the lifetime of Rhodamine B in water was determined from standard frequency-domain phase fluorometry to be 1.5 ns. Furthermore, the lifetimes of the unbound ethidium bromide and bound ethidium bromide to nucleic acid are known to be 1.7 and 24 ns, respectively. Measurements of lifetime in cytoplasm show that there was significant staining of cytoplasmic structures by Rhodamine DHPE. The average lifetime in the nucleus is between that of bound and unbound ethidium bromide indicative of the fact that both populations of the chromophores exist in the nucleus. Nonetheless, the lifetime contribution from bound ethidium bromide is sufficient to distinguish the different lifetimes in the nucleus and cytoplasm as demonstrated by the phase image.

4. Potential for Studying Ultra-fast Molecular Dynamics

Figure 8:
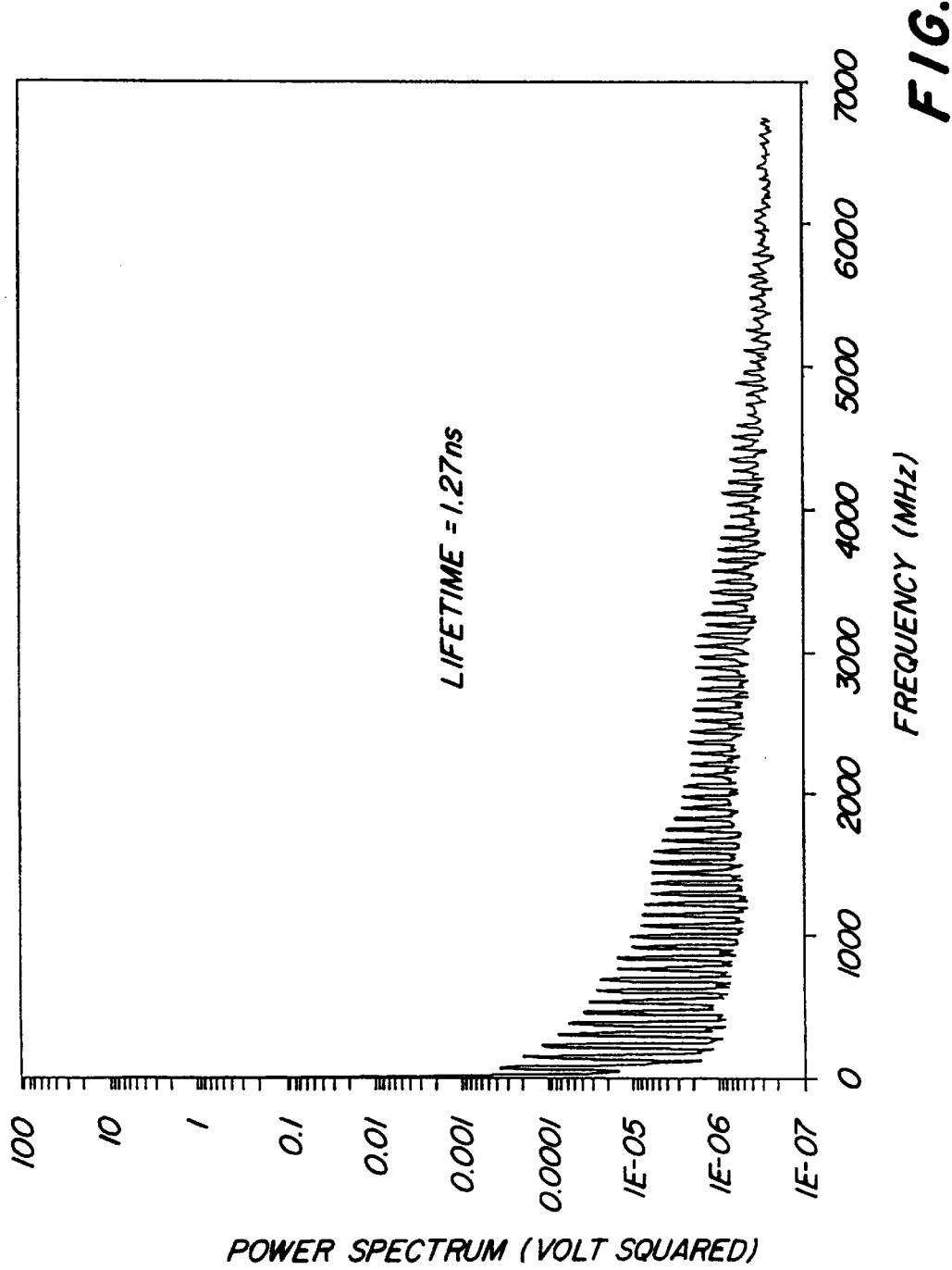
FIG. 8 is a plot of the high frequency spectra of Rhodamine B in water obtained with the microscope system of the present invention.

A slide of 7.8 mM Rhodamine B in water was used to demonstrate the potential of pump-probe fluorescence microscopy in providing lifetime-resolved, high frequency images without a fast optical detector. By using a spectrum analyzer, Rhodamine B's power spectrum was recorded up to about 6.8 GHz (FIG. 8). Note that the harmonics displayed begin at 210 Hz, the first harmonic, and are separated by the same frequency difference of 210 Hz. However, the harmonics actually correspond to the sample's response at harmonics of excitation frequency of 76.2 MHz. The decay in amplitude as the frequency increases corresponds to the decrease in modulation predicted in Eqns. (6). By fitting the harmonics'decay, the lifetime of Rhodamine B in water is determined to be 1.27 ns, in good agreement to 1.5 ns measured by standard frequency-domain phase fluorometry.

FIG. 8 demonstrates the potential of the present invention for obtaining high frequency images of biological systems by measuring the cross-correlation signal at low frequencies. Any harmonic displayed in the figure can be used for imaging purposes.

The pump-probe stimulated emission microscope of the present invention utilizes the fluorescence signal at the cross-correlation frequency, resulting in superior spatial resolution and effective off-focal background rejection compared to conventional one-photon microscopy. Due to the shorter wavelengths used in the one-photon pumping and probing process, this technique has superior spatial resolution compared to corresponding two-photon excitation microscopy, and it has comparable spatial resolution as confocal microscopy. Furthermore, eliminating the need of a fast optical detector for high frequency time-resolved images makes pump-probe microscopy an attractive tool to study fast molecular processes inside cellular structures. While the illustrated embodiment achieves all of these advantages, it will be appreciated by those skilled in the art that changes and modifications may be made thereto without departing from the invention in its broader aspects and as set forth in the following claims.

What is claimed is:

1. A pump-probe fluorescence microscope comprising:
a first amplitude modulated laser modulating at a first amplitude modulation frequency;
a second amplitude modulated laser modulating at a second amplitude modulation frequency;
optical transmission means for combining light output from the first and second amplitude modulated lasers, and for focusing combined light output from the first and second lasers upon a common set of molecules in a sample to stimulate fluorescence emissions from said common set of molecules;
optical collection means for collecting a fluorescence signal emitted from the common set of molecules in response to the focusing of combined light output from the first and second amplitude modulated lasers;
a filter for isolating a cross-correlation signal within said fluorescence signal, said cross-correlation signal having an amplitude modulation frequency approximately equal to the difference between said first and second frequencies; and
signal processing means for obtaining an image based upon said cross-correlation signal.

2. The microscope according to claim 1, wherein said signal processing means further comprises sampling means for obtaining a predetermined number of sampling points per cross correlation signal waveform.

3. The microscope according to claim 2, wherein said predetermined number of sampling points is four.

4. The microscope according to claim 2, wherein said signal processing means further comprises fast Fourier transform means for conducting a fast Fourier transform on a signal output from said sampling means.

5. The microscope according to claim 4, wherein said signal processing means obtains said image from phase characteristics of a signal output from said fast Fourier transform means.

6. The microscope according to claim 4, wherein said signal processing means obtains said image from modulation characteristics of a signal output from said fast Fourier transform means.

7. The microscope according to claim 4, further comprising:

an optical scanner within said optical transmission means, for raster scanning the combined light output focused upon said sample.

8. The microscope according to claim 7, further comprising:

translation means for varying the distance between the sample and said optical transmission means so that depth of focus of the combined light output upon the sample is correspondingly varied.

9. The microscope according to claim 1, wherein said first and second amplitude modulated lasers are sinusoidally modulated at said respective first and second amplitude modulation frequencies.

10. The microscope according to claim 1, wherein the strength of the cross correlation signal is proportional to the spatial integral of the intensity product of pump and probe beams emitted respectively from the first and second amplitude modulated lasers, according to a relationship:

$$\int I(u,v)I'(u',v')d^3t,$$

where pump and probe beam intensity distribution is represented by I(u, v) and I'(u',v'), respectively.

11. The microscope according to claim 1, wherein the wavelength of one of the pump and probe lasers is varied so that said image includes time-resolved spectral image data.

12. A pump-probe fluorescence microscope comprising:

a first amplitude modulated laser modulating at a first amplitude modulation frequency;

a second amplitude modulated laser modulating at a second amplitude modulation frequency;

optical transmission means for combining light output from the first and second amplitude modulated lasers, and for focusing combined light output from the first and second lasers upon a sample;

optical collection means for collecting a fluorescence signal emitted from the sample in response to the focusing of combined light output from the first and second lasers;

signal processing means for obtaining an image based upon said fluorescence signal; and respective separate pump and probe laser polarizers for said first and second amplitude modulated lasers, wherein one of said polarizers varies the polarization of its respective laser so that said image includes time-resolved polarization image data.

13. A pump-probe fluorescence microscope comprising:

a first laser emitting amplitude modulated light at a first amplitude modulation frequency;

a second laser emitting amplitude modulated light at a second amplitude modulation frequency;

a combiner which receives and combines the light from the first and second lasers;

an X-Y scanner receiving light output from said combiner and raster scanning the light output;

an objective lens receiving scanning light from said X-Y scanner, said objective lens focusing said scanning light upon a common set of molecules in a sample to induce fluorescence emissions from said common set of molecules in the sample;

a collection lens disposed to collect said fluorescence emissions;

an optical sensor disposed to receive fluorescence emissions collected by said collection lens, said optical sensor producing a fluorescence signal in response to said fluorescence emission;

an isolation filter, said filter isolating a cross correlation signal between said first and second amplitude modulation frequencies emitted from said common set of molecules;

a digitizer which receives and digitizes the cross correlation signal; and sampling means for obtaining a predetermined number of sampling points per cross correlation signal waveform.

14. The microscope according to claim 13, wherein image data is present in the sampled cross correlation signal and said predetermined number is small enough to permit frame acquisition rates of approximately 3 to 50 seconds for a 256×256 pixel frame.

15. The microscope according to claim 14 further comprising:

fast Fourier transform means for conducting a fast Fourier transform on a signal output from said sampling means.

16. The microscope according to claim 15, further comprising:

a display for displaying said image data, said image data being obtained from a signal output from said fast Fourier transform means; and storage means for storing said image data.

17. A method for microscopic imaging, comprising steps of:

subjecting a common set of molecules in a sample to combined scanned laser light including amplitude modulated pump laser light of a first amplitude modulation frequency, and amplitude modulated probe laser light of a second amplitude modulation frequency;

monitoring cross correlation fluorescence emissions induced in said sample from said common set of molecules in response to said combined laser light at a difference amplitude modulation frequency approximately equal to the difference between the first and second frequencies;

sampling said cross correlation fluorescence emissions to produce a sampled signal;

Fourier transforming the sampled signal; and obtaining image data from the Fourier transformed sampled signal, based upon phase or modulation of the Fourier transformed sampled signal.

18. The method according to claim 17, wherein said difference frequency is smaller than either said first or second frequencies.

* * * * *

UNITED STATES PATENT AND TRADEMARK OFFICE
CERTIFICATE OF CORRECTION

PATENT NO. : 5,814,820
DATED : September 29, 1998
INVENTOR(S) : Dong et al.

It is certified that error appears in the above-identified patent and that said Letters Patent is hereby corrected as shown below:

Column 3, line 12, delete "σis" and insert --σ is-- therefor

Column 5, line 48, delete "FIG." and insert --FIGS.-- therefor

Column 5, line 48, delete "image" and insert --images-- therefor

Column 8, line 47, delete "seanner" and insert --scanner-- therefor

Column 10, line 16, delete "r are" and insert --are-- therefor

UNITED STATES PATENT AND TRADEMARK OFFICE
CERTIFICATE OF CORRECTION

PATENT NO. : 5,814,820
DATED : September 29, 1998
INVENTOR(S) : Dong et al.

It is certified that error appears in the above-identified patent and that said Letters Patent is hereby corrected as shown below:

Column 10, line 24, delete "$\int \Gamma(u',v')^{\Gamma}$" and insert "$\int I(u,v)^{I'}$" therefor Column 10, line 30, delete "$I(u,v)^2$," and insert --$I(\underline{u},\underline{v})^2$,-- therefor Column 10, line 32, delete "$2\ 2$"

Column 11, line 49, delete "1.5 µmW" and insert --1.5 mW-- therefor

Column 12, line 47, delete "Oreg." and insert -- OR). -- therefor

UNITED STATES PATENT AND TRADEMARK OFFICE
CERTIFICATE OF CORRECTION

PATENT NO. : 5,814,820
DATED : September 29, 1998
INVENTOR(S) : Dong et al.

It is certified that error appears in the above-identified patent and that said Letters Patent is hereby corrected as shown below:

Column 13, line 4, delete "long" and insert

--a long-- therefor

Signed and Sealed this

Seventh Day of December, 1999

Attest:

Q. TODD DICKINSON

*Attesting Officer*          *Acting Commissioner of Patents and Trademarks*